(12) United States Patent
Iesaka

(10) Patent No.: US 6,761,741 B2
(45) Date of Patent: Jul. 13, 2004

(54) PROSTHETIC JOINT

(76) Inventor: Kazuho Iesaka, 331 E. 17th St., New York, NY (US) 10003

( * ) Notice: Subject to any disclaimer, the term of this patent is extended or adjusted under 35 U.S.C. 154(b) by 0 days.

(21) Appl. No.: 10/411,773

(22) Filed: Apr. 10, 2003

(65) Prior Publication Data

US 2003/0229398 A1 Dec. 11, 2003

Related U.S. Application Data

(63) Continuation-in-part of application No. 10/166,490, filed on Jun. 10, 2002, now abandoned.

(51) Int. Cl.[7] .................................................. A61F 2/32
(52) U.S. Cl. .............................. 623/22.26; 623/22.11; 623/22.13; 623/22.21
(58) Field of Search .................... 623/22.13, 22.15, 623/22.14, 22.21, 22.4, 22.26

(56) References Cited

U.S. PATENT DOCUMENTS 3,864,758 A * 2/1975 Yakich ..................... 623/22.13
5,514,182 A * 5/1996 Shea ......................... 623/23.4
5,935,171 A * 8/1999 Schneider et al. ....... 623/22.15

OTHER PUBLICATIONS

Saunders, Fenella. Self–Healing Plastics, May 2201, Discover, vol. 22 No. 5, entire article.*

* cited by examiner

*Primary Examiner*—David J. Isabella
*Assistant Examiner*—Kamrin R. Landrem
(74) *Attorney, Agent, or Firm*—Muserlian, Lucas and Mercanti

(57) ABSTRACT

A prefabricated joint is employed for the prosthetic joint. The joint includes prefabricated socket, ball, and capsule. The capsule is attached from the ball to the socket. The capsule seals the area between the ball and socket and prevents wear debris from entering the body cavity. In the case of the hip joint, the doctor need only attach the prefabricated unit to the femoral unit to connect the prosthetic joint after the prefabricated unit and femoral unit have been placed into the acetabular and femur, respectively.

16 Claims, 6 Drawing Sheets

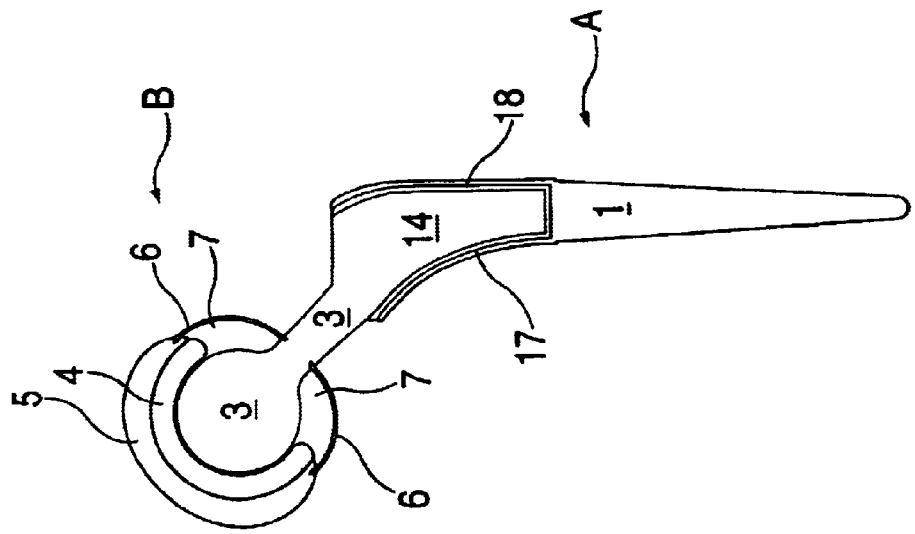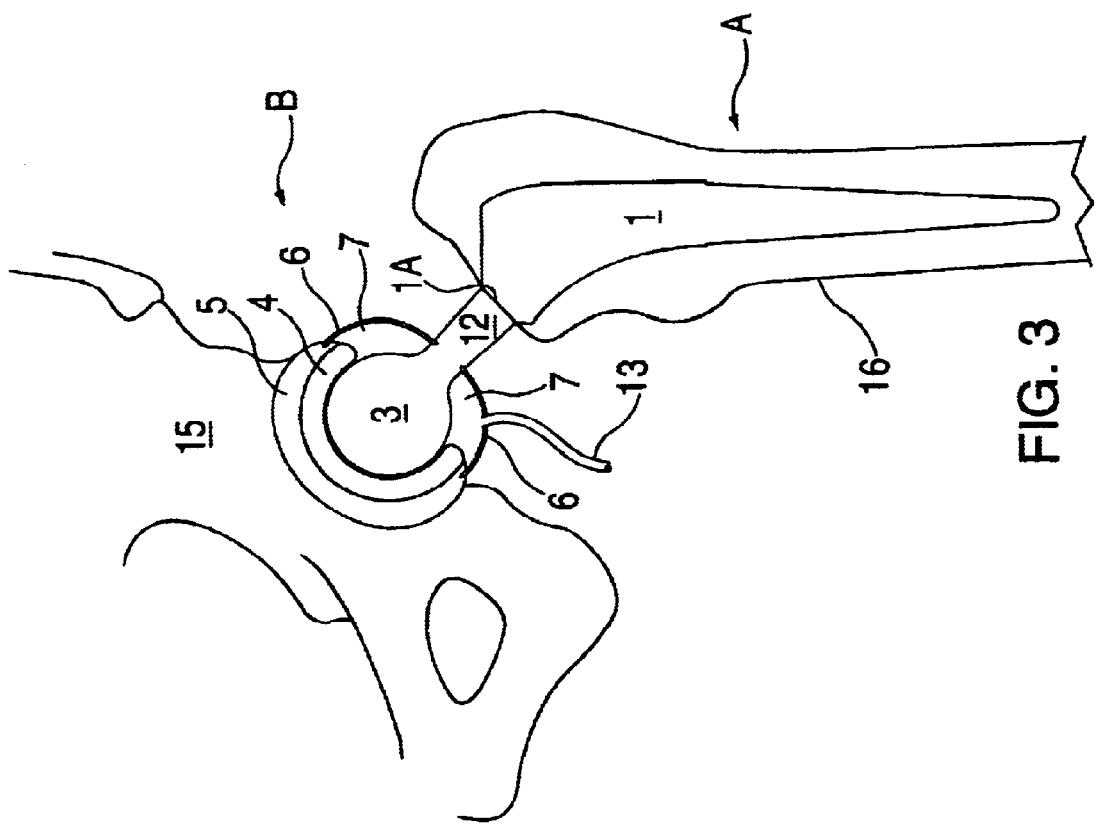

PROSTHETIC JOINT

CROSS REFERENCE TO RELATED APPLICATIONS

This Application is a Continuation-in-part of U.S. patent application Ser. No. 10/166,490 filed Jun. 10, 2002, now abandoned.

BACKGROUND OF THE INVENTION

1. Field of the Invention

This invention relates to a prosthetic joint and, more particularly, to a prosthetic hip joint which prevents particulate debris generated from the joint from entering the body cavity and prevents debris from the body cavity entering the joint.

2. Art Relating to the Invention

Prosthetic joints are well-known devices and, in the case of a hip joint, comprise an acetabular component which is affixed to the acetabulum, i.e. hip bone, and a femoral component, affixed to the femur bone. The acetabular component comprises a socket which is affixed to the acetabulum and a ball that rotates within the socket. The femoral component comprises a stem which is affixed to the femur and a neck which is affixed to the ball. Typically, the socket is divided between an outer cup that faces the acetabulum and an inner cup that faces the ball. The inner cup of such joints is typically made of polyethylene while the outer cup is made of a metal alloy or a ceramic material. The ball is made of a metal, metal alloy or ceramic material.

One of the problems associated with prosthetic joints is wear debris, namely polyethylene wear debris generated from the interface between the ball and the socket and the interface between the inner cup and the outer cup. This wear debris finds its way into the human cavity and causes inflammation. Inflammation can cause bone destruction as well as weakening of the bond between the prosthesis and the bone.

Another problem is body debris generated from the body cavity finding its way into the joint and interfering with the joint. Body debris such as bone pieces can find their way into the joint and cause excessive wear or damage to the joint.

To prevent debris from leaving the junction between the outer cup and the acetabulum and the junction between the stem and the femur, it has been suggested that a barrier or capsule be placed over each of these junctions, see U.S. Pat. No. 5,735,900. It has also been suggested that a barrier or capsule extend over only the junction between the stem and the femur bone, see U.S. Pat. Nos. 5,899,942 and 6,132,470.

For preventing debris from leaving the interface of the ball and the socket, it has been suggested to employ a flexible capsule which extends from the ball where it affixes to the stem to the outside of the socket where it is affixed to the hip bone, see U.S. Pat. Nos. 3,739,403; 4,731,088; 4,822,368; 5,514,182; 5,702,483; and 5,755,807.

Typically, a prosthetic hip joint comes in different size sockets, balls and stems, all of which are separate and all of which are selected and assembled by the doctor during the replacement operation. The selection is based on the size of the patient.

Typically, the doctor, during the operation performs the following steps in sequential order: selects an inner cup, an outer cup, a ball and a stem; affixes the outer cup to the hip bone; affixes the inner cup to the outer cup; affixes the stem to the femur; affixes the ball to the stem; and finally, places the ball in the socket. If a capsule is used, the capsule is set in place at the very end.

As will be appreciated, so many different sized parts which must be assembled during the operation increase the duration and complexity of the operation. Also, because the capsule is affixed at the end of the assembly, it may not be strongly adhered.

SUMMARY OF THE INVENTION

It has now been discovered that debris contamination problems can be solved by employing a preformed ball and socket with a capsule already attached thereto. Such a preformed unit is assembled at the factory rather than by the doctor in the operating room.

Additionally, by employing an already preformed encapsulated ball and socket, the time and complexity of the operation is also reduced.

Such a preformed acetabular component comprising a ball-socket-capsule unit means that the manufacturer makes the preformed unit with different sized sockets and different sized balls. Thus, the doctor need only size the socket and the stem to the patient's bone structure. The step of assembling the socket, matching the ball and the socket and affixing the capsule between the ball and the socket has already been performed by the factory. This increases the strength of the bond between the capsule and the ball and socket as well as simplifies the overall operation.

Broadly, the present invention is an improvement in a prosthetic hip joint, wherein the improvement comprises:
  a preformed acetabular component comprising:
    (1) a socket adapted for attachment to an acetabulum;
    (2) a ball with a first attachment member, said ball rotatably positioned within said socket, said first attachment member facing outward away from said socket; and
    (3) a flexible joint capsule attached to said ball adjacent said first attachment member and to said socket, said capsule preventing wear debris from escaping from a joint between said ball and socket and preventing body debris from entering said joint and said capsule attached to said socket so as to avoid interference between the attachment of said socket to said acetabulum.

In the case of total hip replacement, the present invention further comprises:
  a femoral component having a stem for attachment to a femur, and a second attachment member that mates with said first attachment member wherein said preformed acetabular component is attached to said femoral component by mating said first and second attachment members. Preferably, the mating of the first and second attachment members occurs after said preformed acetabular component has been affixed to an acetabulum and said femoral component has been affixed to a femur.

The capsule isolates the joint cavity and prevents debris from the ball and socket from entering the body cavity. Also, the capsule prevents body debris from entering the joint and causing damage to the joint.

Also, because the capsule is formed on the ball and socket in the factory rather than in the operating room, a very strong seal is made between the capsule and the ball and socket. As such, it provides strength to the ball and socket joint itself, thereby helping to prevent dislocation of the joint itself.

Also, the capsule can prevent body debris such as body fragments (like the ones which are produced during surgery), or cement debris, or metal debris from entering the ball and socket interface. It is known that if polyethylene is used to make the inner cup and the inner cup is scratched by such body debris, wear of polyethylene will progress faster than normal.

Furthermore, the space defined by the capsule and the ball and socket can be filled with different types of fluids to promote ease of movement between the ball and the socket, to prevent entrapment of the capsule in the joint between the ball and the socket, and to provide a self-healing or repair mechanism to the joint.

In surface replacement type hip prosthetics, the ball has a peg which is affixed directly into the femur bone. The top of the femur bone is cut to mate with the ball and drilled to accommodate the peg. In surface replacement type hip prosthetics, the peg is part of the ball. For surface replacement type hip prosthetics made in accordance with the present invention, the peg forms the first attachment member. Alternatively, if the ball has a cup section which surrounds the femur bone, then this cup forms the first attachment member.

Preferably, the socket has an inner and an outer cup and the capsule is affixed to either the inner or the outer cup. Where the socket has both an inner and an outer cup, the capsule also prevents debris from entering or leaving the joint between the inner and outer cup when the capsule is affixed to the outer cup.

BRIEF DESCRIPTION OF THE DRAWINGS

These and other aspects of the present invention may be more fully understood by reference to one or more of the following drawings wherein:

FIG. 3 illustrates yet another embodiment of the present invention;

FIG. 4 illustrates still another embodiment of the present invention;

DETAILED DESCRIPTION OF THE INVENTION

Figure 1:
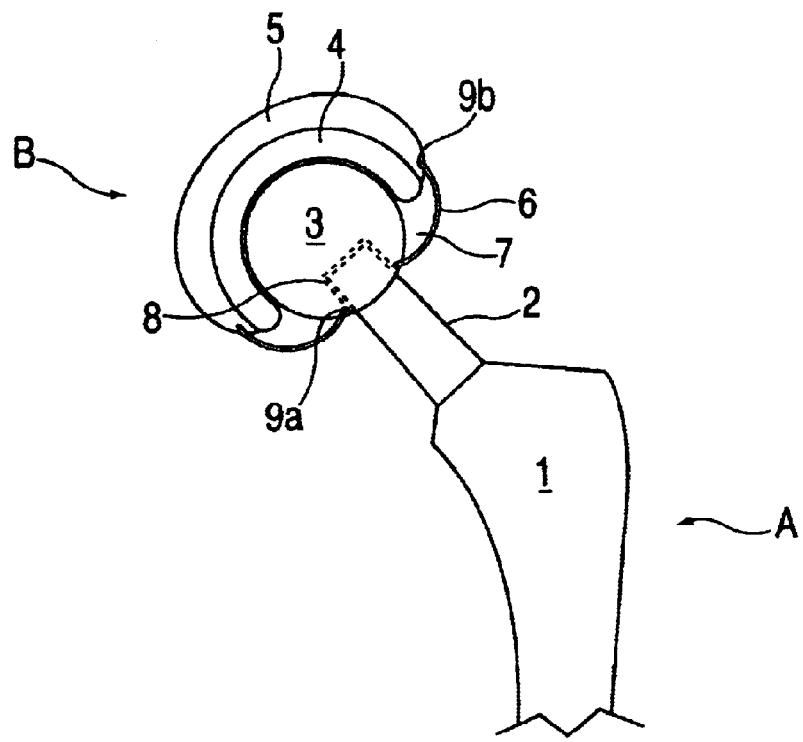
FIG. 1 illustrates one embodiment of the present invention.

As shown in FIG. 1, the hip joint of the present invention has femoral component A which comprises femoral stem 1 and femoral neck 2. Preformed acetabular component B comprises ball 3, inner acetabular cup 4, outer acetabular cup 5 and capsule 6. Ball 3 resides and rotates within inner acetabular cup 4 and outer acetabular cup 5. The two acetabular cups 4 and 5 make up the socket. Joint capsule 6 is affixed to outer acetabular cup 5 of the socket and to ball 3. Joint capsule 6 closes off an isolated joint cavity 7. Cavity 7 collects debris from the wear of ball 3 and inner acetabular cup 4 and wear debris from between acetabular cups 4 and 5. Ball 3 has a cavity 8 in which femoral neck 2 is affixed to ball 3. Cavity 8 is a first attachment member and femoral neck 2 is a second attachment member.

Outer cup 5 need not be affixed to acetabulum 15 (FIG. 3). This allows cup 5 to rotate within acetabulum 15. Usually, this type of hip prosthetic is called "bipolar" because of the two rotational surfaces, one between acetabulum 15 and cup 5 and the other between cup 4 and ball 3.

The factory forms the acetabular components of ball 3, outer and inner acetabular cups 4 and 5, and joint capsule 6. The size of the outer acetabular cup 5 is varied to accommodate different sizes of hips.

In order to affix capsule 6 to ball 3, groove 9a can be formed around cavity 8. Grooves 9b are used to secure capsule 6 to cup 5. The edge of capsule 6 is inserted into groove 9a and affixed into groove 9a by a conventional means such as crimping or gluing with an adhesive composition. Likewise, the other edge of capsule 6 is affixed to groove 9b in outer acetabular cup 5 in a conventional manner such as by gluing or crimping. Groove 9b is placed in cup 5, at its edge, to provide for affixing or crimping capsule 6 to cup 5.

The femoral component is made as a separate piece from the acetabular component. Femoral neck 2 and cavity 8 are mated or affixed to one another by conventional means such as screw threads, taper lock, and/or an adhesive composition.

Figure 2:
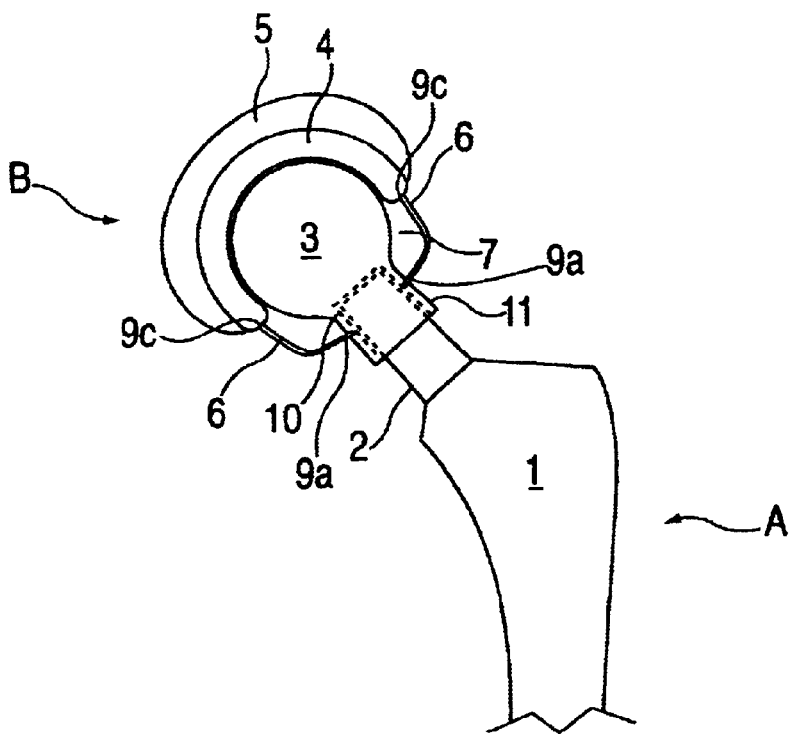
FIG. 2 illustrates another embodiment of the present invention.

FIG. 2 illustrates another embodiment of the present invention wherein the femoral component has femoral stem 1 with femoral neck 2 which fits into corresponding cavity 10 in ball 3, and ball 3 has a neck 11 which extends outward from ball 3 and is positioned adjacent cavity 10 for encompassing neck 2. Neck 11 is part of ball 3 and the prefabricated hip section. Capsule 6 is affixed to neck 11 and inner cup 4 by grooves 9a and 9c in a conventional manner. Neck 11 with cavity 10 form a first attachment member while neck 2 is a second attachment member.

FIG. 3 illustrates yet another embodiment of the present invention wherein ball 3 has a solid neck 12 without a cavity therein. In this embodiment, neck 12 is affixed to the femoral component at face 1A. Neck 12 is a first attachment member while face 1A is a second attachment member. Capsule 6 is affixed to the outside of neck 12 and to cup 5. Suitably, a groove or channel is placed in neck 12 and cup 5 to affix capsule 6 thereto. Also as shown in FIG. 3, capsule 6 can have a feeder tube 13 through which liquid is introduced into or removed from cavity 7. Tube 13 can also be used to flush or clean cavity 7 to remove wear debris.

In FIG. 4, neck 14 of ball 3 is sized to fit into pocket 17 of femoral component A. Pocket 17 mates with neck 14. Preferably, a shock absorbing material 18 is glued in place between pocket 17 and neck 14. In this embodiment, neck 14 forms a first attachment member and pocket 17 forms a second attachment member.

Figure 5:
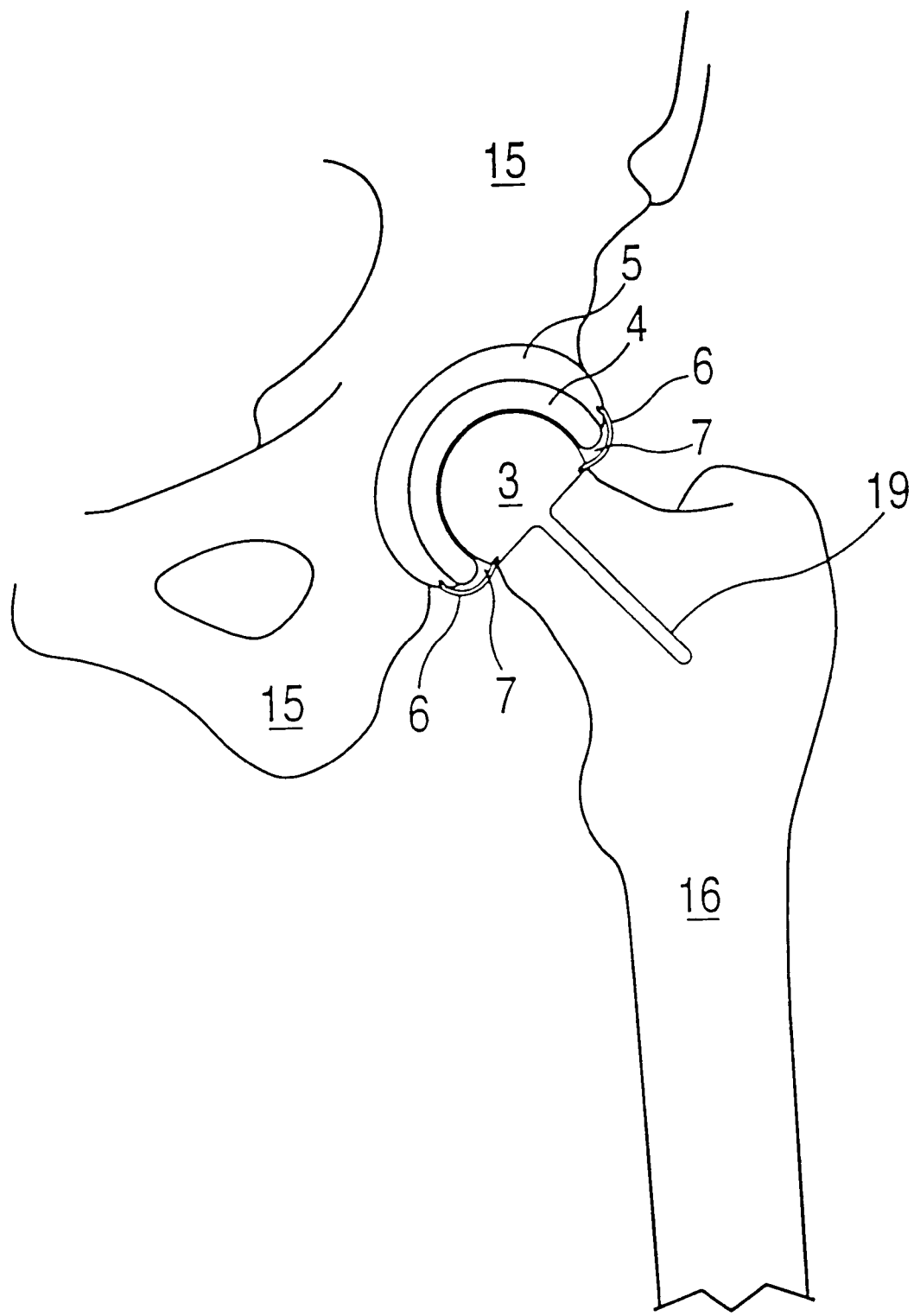
FIG. 5 illustrates the ball with a stem for affixing directly to the femur bone for surface replacement.

FIG. 5 illustrates yet another embodiment of the present invention wherein ball 3 has stem 19 and ball 3 is directly affixed to femur 16. This type of prosthesis is called "surface replacement" type. Ball 3 is affixed to femur 16 in a conventional manner using conventional bone cement or by means of press fit. The factory preforms the acetubular components of ball 3 including stem 19, outer and inner acetabular cups 4 and 5, and joint capsule 6. Stem 19 is the first attachment member.

As can be seen in FIGS. 1–5, cavity 8, necks 11, 12 and 14 and stem 19 form part of ball 3, and ball 3 is prefabricated with inner and outer acetabular cups 4 and 5 and capsule 6.

Outer acetabular cup 5 is fixed into acetabulum 15 in a conventional manner using conventional bone cement or by means of press fit. Stem 1 is fixed to femur 16 in a conventional manner using conventional bone cement or by means of press fit. Additionally, shock absorbing material can be used between the bone and the prosthetic joint. Such shock absorbing material includes silicone, plastic materials and rubber. Shock absorbing layer 18 is especially suitable for use between neck 14 and pocket 17 as shown in FIG. 4.

The sizing of the prefabricated acetabular component, outer acetabular cup 5 in acetabulum 15, and sizing of the femoral component in femur 16 is done in a conventional manner using conventional equipment. Suitably, a groove is formed in both ball 3, or a part thereof, and in cups 4 or 5 to affix capsule 6.

Figure 6:
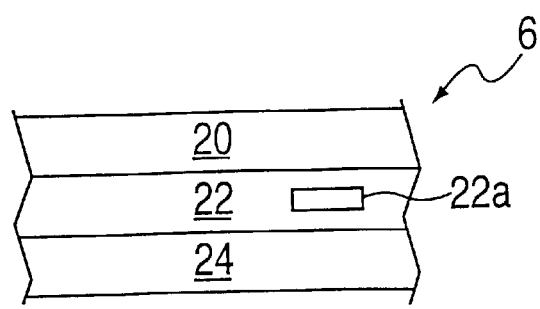
FIG. 6 illustrates a cross-section of the capsule.

FIG. 6 illustrates a preferred arrangement of capsule 6 which comprises inner layer 20, middle layer 22 and outer layer 24. Inner layer 20 faces towards ball 3 while outer layer 24 faces the body cavity and stem 1. Preferably, when all three layers are present, inner layer 20 acts as an absorbent of debris from inside the prefabricated acetabular component. Suitable materials for use as an absorbent include HEPA® (High Efficiency Particle Absorbing) filter (HEPA Corporation, Anaheim, Calif.).

Capsule 6 need not be impermeable to all things. It can act as a filter or net to trap or absorb debris and prevent, or at least decrease, the amount of debris which travels into and out of cavity 7. As is known, inflammation due to debris, osteolysis, is dose dependent. Thus, decreasing the flow of wear debris out of cavity 7 will help alleviate problems.

Outer layer 24 is an optional layer comprising an antibreak, antishock and antiwear material which can be made from an elastic material which is solid or woven. Suitable materials for use as outer layer 24 include nylon fabric, glass fiber fabric, metal fiber fabric, rubber, silicone and GORETEX®, for example.

Middle layer 22 is an optional layer which is primarily for antishock. Middle layer 22 can also have elastic memory to hold or keep the capsule in regular form. Suitable materials for use as middle layer 22 include rubber, plastic, and silicone.

Sensor 22a can be placed in middle layer 22 to monitor temperature, pressure and pH. An IC chip can be placed in this layer also for storing information about the joint. Sensors can be placed anywhere in the joint capsule but it is preferred to place the sensors in the middle layer to facilitate its sensing ability and protect it from physical stress. The chip can be placed anywhere in the joint system but it is preferred that the chip be close to the exterior of the capsule to facilitate communication to the outside of the body. Such sensors are conventional and are available from FOP-M in-vivo ultra-miniature pressure sensors, see U.S. Pat. Nos. 5,392,119 and 5,202,939. Fisco Technologies Ste-Foy, Quebec, Canada and MEMS sensor series, Integrated Sensing Systems Ypsilanti, Mich., USA.

The capsules primary function is to prevent debris from passing, either into the body cavity or into the joint cavity of the preformed acetabular component. The capsule must be able to keep molecular size wear debris from entering the body cavity as much as possible. Such debris generally has a size of about 0.5 to about 100 microns. Because the intensity of the inflammatory reaction of human body against wear debris depends on the amount of wear debris released, the capsule can work as a filter or absorbent of wear debris and decrease the intensity of the reaction even if complete sealing of wear debris is not possible.

Capsule 6 must have some elastic properties to allow for movement of ball 3 in the socket and to hold capsule 6 away from the joint.

Figure 7:
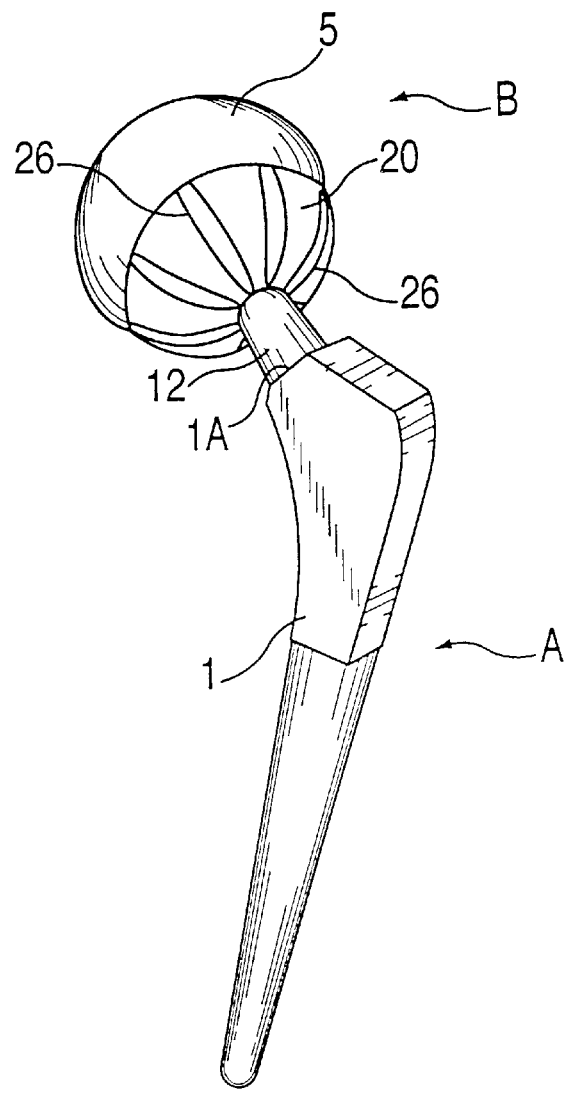
FIG. 7 illustrates an alternative design for the capsule.

FIG. 7 illustrates a flame design for capsule 6 wherein strips or flames 26 are employed on the outside of inner layer 20. Flames 26 are elastic material which help hold capsule 6 out, away from the joint, so that capsule 6 does not impinge on the movement of the joint. FIG. 7 illustrates flame 26 attached on the outside of inner layer 20, however, flames 26 can also be attached to the inside of inner layer 20 or into middle layer 22 or outer layer 24. Flames 26 help maintain the capsule in proper form.

Figure 8A:
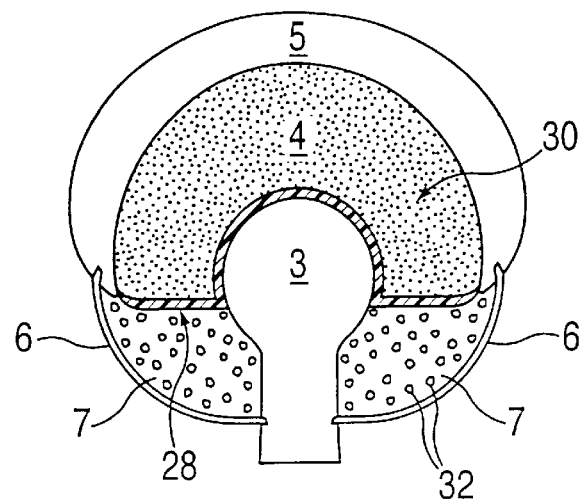
FIGS. 8A–8G illustrate the repair mechanism of the present invention.
Figure 8B:
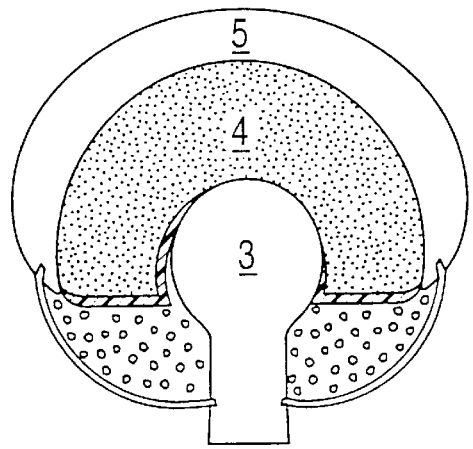
Figure 8C:
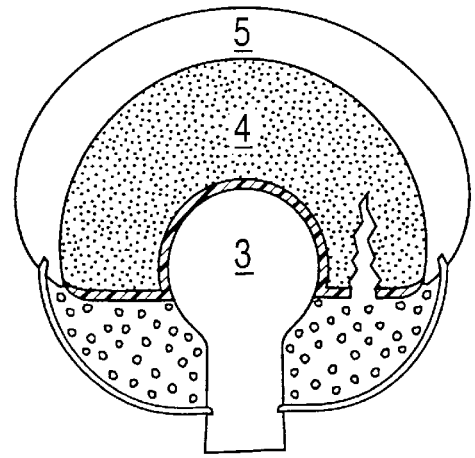
Figure 8D:
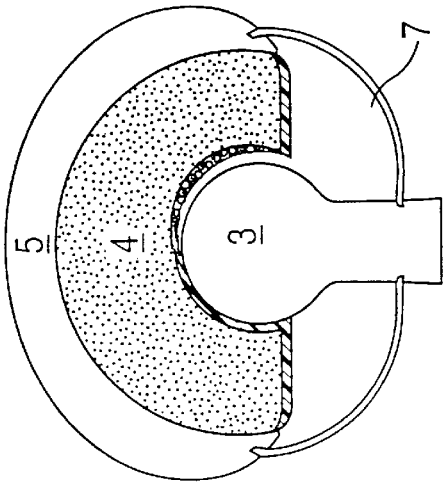
Figure 8E:
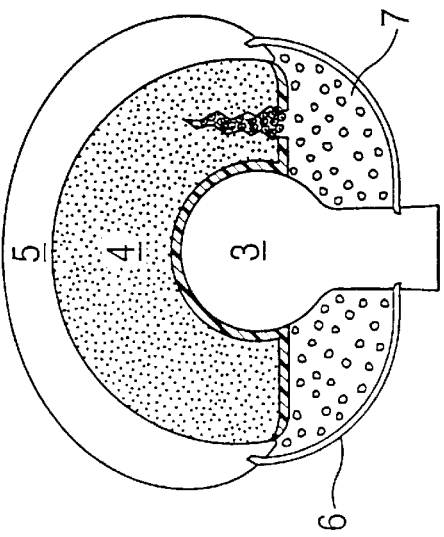
Figure 8F:
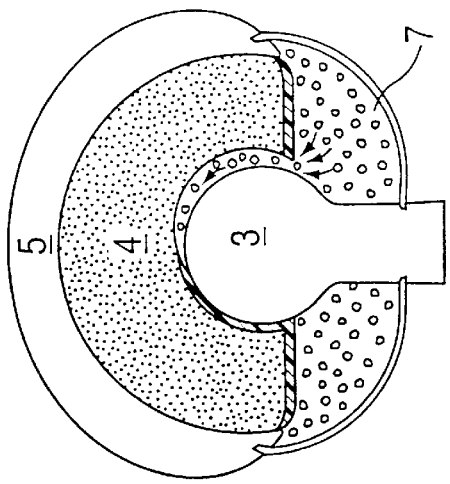
Figure 8G:
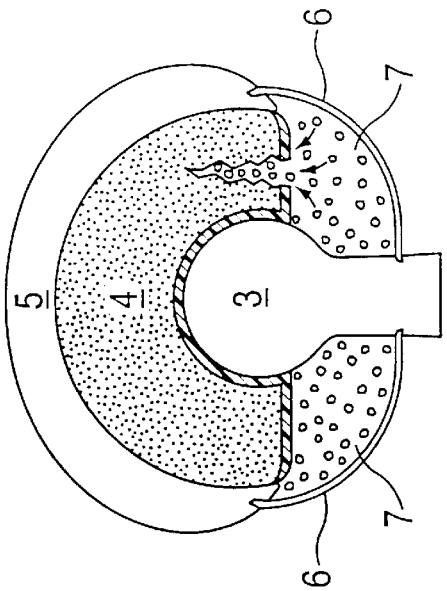

FIGS. 8A–8G teach the self-healing aspect of the present invention. In this embodiment, the inner cup 4 is made of polyethylene and has embedded in it polyethylene catalyst 30. In cavity 7 monomers 32 are suspended in a suitable fluid. When a wear spot occurs in surface coating 28 as shown in FIG. 8B or a crack occurs in cup 4 as shown in FIG. 8C, monomers 32 flow into the area as shown in FIGS. 8D and 8E. Because catalyst 30 is embedded in cup 4, monomers 32 react to form a polymer in the area that the catalyst is present as shown in FIGS. 8F and 8G, respectively. Since catalyst 30 is embedded in cup 4, it does not escape into cavity 7 to cause all of monomer 32 to polymerize. The catalyst and monomer are mated so that the catalyst causes the monomer to polymerize. Suitable monomers are ethylene and propylene. Suitable catalysts are Ziegler-Natter Catalysis and Metallocene Catalysis.

It will be appreciated that monomer 32 can be embedded in cup 4 while catalyst 30 is in a fluid in cavity 7.

For the self-healing aspect of the present invention, capsule 6 must maintain the fluid and either monomers 32 or catalyst 30 in cavity 7.

Preferably, the point of attachment of capsule 6 to necks 11, 12 and 14 is far enough away from ball 3 to prevent impingement of the neck or inner or outer acetabular cups 4 and 5 on capsule 6. Also, the elasticity of capsule 6 is such to mitigate damage to capsule 6. This must take into account the range of motion of a hip joint. Normally, a hip joint has 170° of movement, therefore, it is preferred that the capsule allow for 200° of movement.

Suitably, cavity 7 can be filled with a monomer or catalyst for self-healing, and/or a lubricant by the factory. Alternatively, such fluids can be inserted into cavity 7 through tube 13 (FIG. 3). The liquid can be a lubricant or it can be a fluid compatible with body fluid such as water or a saline solution. The fluid plays two roles, it helps prevent wear and it also acts to prevent the joint capsule from becoming entrapped between the neck, ball 3 and inner and outer acetabular cups 4 and 5. The lubricant can be a silicone, oil, gel, or polymer, and it can contain a surface protective substance such as MICROLON®. The fluid can also contain monomers, catalyst or other chemicals which repair the worn joints as well as protect the surface of the joint that is inside the capsule.

It is also known that polyethylene degenerates by oxidation in the human body. Thus, it can be beneficial to add an anti-oxidant into the fluid in the joint. This helps to avoid or minimize the oxidation of the polyethylene.

In the detailed description, two cups, inner cup 4 and outer cup 5, have been disclosed. However, both can be formed into a single cup or socket for use in the present invention.

In the detailed description, the outer cup has been disclosed as it has been affixed to the acetabulum (hip bone). However, the outer cup can move within the acetabulum to develop the second rotating surface between the acetabulum and the outer cup. This type of prosthesis is usually called "bipolar type" because this type has two rotation surfaces, one between the outer cup 5 and acetabulum (hip bone) 15 and the other between inner cup 4 and ball 3.

The femoral component can be made in a conventional manner using conventional material. Typically, femoral components are made of a titanium alloy or a cobalt chromium alloy.

The ball is made in a conventional manner using conventional material such as a titanium alloy, a cobalt chromium alloy, or ceramic.

The outer and inner cups are also made in a conventional manner using conventional materials such as titanium alloy, cobalt chromium alloy, ceramic or polyethylene.

It will be understood that the claims are intended to cover all changes and modifications of the preferred embodiments of the invention herein chosen for the purpose of illustration which do not constitute a departure from the spirit and scope of the invention.

What is claimed is:

1. In a prosthetic hip joint, the improvement comprising:
   a preformed acetabular component comprising:
   (1) a socket adapted for attachment to an acetabulum;
   (2) a ball with a first attachment member, said ball rotatably positioned within and in direct contact with said socket and said first attachment member facing outward away from said socket; and
   (3) a flexible joint capsule attached to said ball adjacent said first attachment member and to said socket, said capsule preventing debris from escaping from a joint between said ball and socket and preventing body debris from entering said joint.

2. The joint of claim 1 further comprising a femoral component having a stem for attachment to a femur, and a second attachment member that mates with said first attachment member wherein said preformed acetabular component is attached to said femoral component by mating said first and second attachment members.

3. The joint of claim 1 wherein said socket comprises an inner cup and an outer cup and said capsule is affixed to said outer cup.

4. The joint of claim 1 wherein said socket comprises an inner cup and an outer cup and said capsule is affixed to said inner cup.

5. The joint of claim 2 wherein said first attachment member is a cavity in said ball and said second attachment member is a femoral neck which fits into said cavity.

6. The joint of claim 2 wherein said first attachment member is a neck with a cavity therein, and said second attachment member is a femoral neck which mates with said cavity.

7. The joint of claim 2 wherein said first attachment member is a neck and said second attachment member is a face that affixes directly to said neck.

8. The joint of claim 2 wherein said first attachment member is a neck stem and said second attachment member is a cavity which mates with said neck stem.

9. The joint of claim 1 wherein said first attachment member is a stem which attaches to a femur bone.

10. The joint of claim 1 further comprising a fluid held in by said capsule in a joint cavity.

11. The joint of claim 1 further comprising a tube positioned in said capsule.

12. The joint of claim 10 wherein a monomer is contained in said fluid and a catalyst is embedded in said socket.

13. The joint of claim 10 wherein a catalyst is contained in said fluid and a monomer is embedded in said socket.

14. The joint of claim 1 further comprising a sensor positioned in said capsule.

15. The joint of claim 8 wherein a shock absorbing material is contained within said cavity between said cavity and said neck stem.

16. The joint of claim 1 further comprising strips of elastic material on the outside of said capsule.

* * * * *